(12) United States Patent  (10) Patent No.: US 7,673,638 B1
Boynton et al.  (45) Date of Patent: Mar. 9, 2010

(54) SYSTEM AND METHOD TO MONITOR PARTICLES REMOVED FROM A COMPONENT

(75) Inventors: Rudy C. Boynton, San Jose, CA (US); Patrick E. Flynn, Gilroy, CA (US); Paul W. Webb, San Jose, CA (US); Gary W. Knoth, Morgan Hill, CA (US)

(73) Assignee: Western Digital Technologies, Inc., Lake Forest, CA (US)

( * ) Notice: Subject to any disclaimer, the term of this patent is extended or adjusted under 35 U.S.C. 154(b) by 889 days.

(21) Appl. No.: 11/454,734

(22) Filed: Jun. 16, 2006

(51) Int. Cl.
*B08B 7/00* (2006.01)
(52) U.S. Cl. .................. 134/94.1; 134/95.3; 134/103.2
(58) Field of Classification Search ........................ None
See application file for complete search history.

(56) References Cited

U.S. PATENT DOCUMENTS 5,315,793 A  5/1994  Peterson et al.
6,740,893 B1*  5/2004  Tanabe ..................... 250/492.2
7,297,286 B2*  11/2007  Tannous et al. ............... 216/58
7,442,112 B2*  10/2008  Yoon .............................. 451/8

* cited by examiner

*Primary Examiner*—Duy-Vu N Deo
(74) *Attorney, Agent, or Firm*—Blakely, Sokoloff, Taylor & Zafman

(57) ABSTRACT

Disclosed is a system and method to monitor and count particles removed from a component. The particle monitoring system includes a jet spray device, a snow generator, a particle collection device, and a particle counter. The jet spray device includes an outlet that is disposed locally relative to the component. The snow generator is operable to generate cleaning snow comprising a stream of ice particles, wherein the cleaning snow is emitted from the outlet of the jet spray device onto the component to cause the ejection of particles from the component. The particle collection device includes a collector that is disposed locally around the component to collect particles ejected from the component. The particle counter is coupled to, and in fluid communication with, the particle collection device. The particle counter is operable to detect and count particles ejected from the component.

33 Claims, 4 Drawing Sheets

SYSTEM AND METHOD TO MONITOR PARTICLES REMOVED FROM A COMPONENT

BACKGROUND

1. Field of the Invention

The present invention relates to a system and method to monitor particles removed from a component.

2. Description of the Prior Art and Related Information

Precision optical, mechanical, and electronic components for use in electro-optical, electro-mechanical, electronic systems, and combinations thereof, need to be cleaned prior to assembly, in order to reduce the amount of contaminant particles that are introduced into these often highly sensitive systems. Further, it is important to be able to monitor, count, and characterize removed contaminant particles from the components that are utilized in such systems. This is especially true for highly sensitive storage systems, such as disk drives.

Today, many contaminant particle removal and monitoring systems utilize liquid solvents and ultrasonic energy in order to remove and monitor contaminant particles. For example, in these types of systems, a component is typically suspended in a liquid solvent and ultrasonic energy is applied to remove particles from the component. The solvent is then processed through a liquid particle counter for the counting, measurement, and binning of the various removed contaminant particles based upon particle size. This information may then be analyzed such that the number and sizes of contaminant particles removed from a particular component can be characterized.

Unfortunately, this commonly-used liquid solvent method, which utilizes ultrasonic energy, is frequency and power dependent and may either be ineffective at particle removal and/or may erode the very component that is being cleaned. Further, this type of liquid solvent particle removal process for a component does not correlate well to the actual particle release from the component in the system as occurs in normal operation. Moreover, the use of liquid solvents, such as chlorofluorocarbons and ketones, are environmentally hazardous and require numerous environmental safety procedures.

SUMMARY

The present invention relates to a system and method for monitoring particles removed from a component.

In one embodiment of the present invention, a particle monitoring system to monitor particles removed from a component is disclosed. The particle monitoring system includes a jet spray device, a snow generator, a particle collection device, and a particle counter. The jet spray device includes an outlet that is disposed locally relative to the component. The snow generator is operable to generate cleaning snow comprising a stream of ice particles, wherein the cleaning snow is emitted from the outlet of the jet spray device onto the component to cause the ejection of particles from the component. The particle collection device includes a collector that is disposed locally around the component to collect particles ejected from the component. The particle counter is coupled to, and in fluid communication with, the particle collection device. The particle counter is operable to detect and count particles ejected from the component.

In another embodiment of the present invention, a method to remove particles from a component and to count the particles removed from the component is disclosed. The method comprises: generating cleaning snow comprising a stream of ice particles; emitting the cleaning snow locally onto the component to cause the ejection of particles from the component; collecting particles ejected from the component locally around the component; detecting particles ejected from the component; and counting particles ejected from the component.

In yet another embodiment of the present invention, a particle monitoring system to monitor particles removed from a component is disclosed. The particle monitoring system includes a jet spray device, a snow generator, a particle collection device, a robotic X-Y table, a heat source, and a particle counter. The jet spray device includes an outlet that is disposed locally relative to the component. The snow generator is configured to generate a continuous stream of cleaning snow including ice particles, wherein the cleaning snow is emitted from the outlet of the jet spray device onto the component to cause the ejection of particles from the component. The particle collection device includes a collector that is disposed locally around the component to collect particles ejected from the component. The robotic X-Y table includes a holding platform to hold the component and the robotic X-Y table is configured to allow for the movement of the jet spray device and the particle collection device in bi-directional horizontal directions relative to the component. The heat source is used to heat the component. The particle counter is coupled to, and in fluid communication with, the particle collection device. The particle counter is operable to sample a pre-defined volume of gas from the particle collection device and to detect and count particles ejected from the component.

The foregoing and other features of the invention are described in detail below and are set forth in the appended claims.

DETAILED DESCRIPTION

In the following description, numerous specific details are set forth. However, it is understood that embodiments of the invention may be practiced without these specific details. In other instances, well-known circuits, structures, and techniques have not been shown in order not to obscure the understanding of this description.

Figure 1:
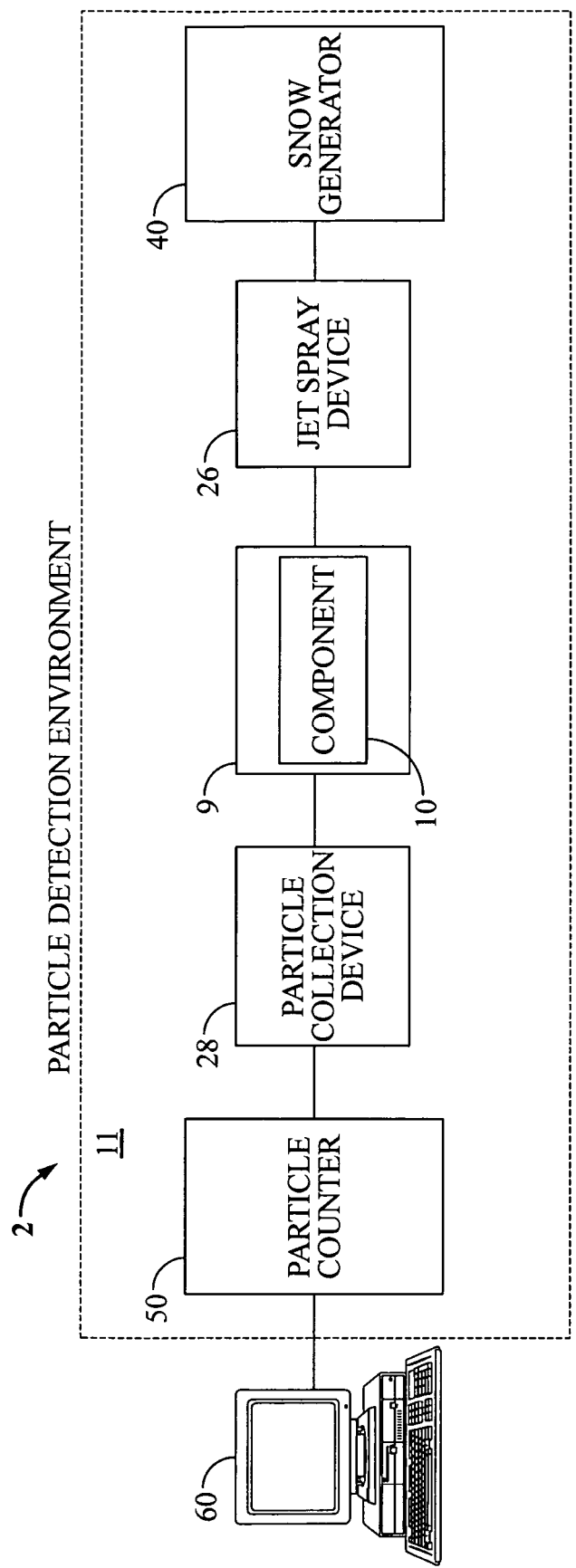
FIG. 1 is a block diagram of a particle monitoring system to monitor and count particles removed from a component, according to one embodiment of the present invention.

With reference now to FIG. 1, FIG. 1 is a block diagram of a particle monitoring system 2 to monitor and count particles removed from a component, according to one embodiment of the present invention. In particular, the particle monitoring system 2 may include a particle detection environment 11 and, optionally, a computer 60.

The particle detection environment 11 may include a holding platform 9 to hold a component 10 to be cleaned. Further, the particle detection environment 11 may include a jet spray device 26 having an outlet that is disposed locally relative the component 10 and a snow generator 40 that is operable to generate cleaning snow comprising a stream of ice particles. The cleaning snow may be emitted from the outlet of the jet spray device 26 onto the component 10 to cause the ejection of particles from the component. A particle collection device 28 may include a collector that is disposed locally around the component to collect particles ejected from the component. A particle counter 50 may be coupled to the particle collection device 28 to detect and count particles ejected from the component.

Additionally, a computer 60 may optionally be coupled to the particle counter 50 in order to characterize information related to the particles counted by the particle counter 50. Particularly, computer 60 may be configured to detect particle count signals received from the particle counter 50 over a suitable connection and interface, in which each particle count signal corresponds to a particle detected by the particle counter 50. For example, based upon received particle count signals for one or more particular components that are cleaned, computer 60 may characterize this data to determine if the individual component, or the plurality components, on average, are sufficiently clean enough to be used in higher-level assemblies for which they are to be assembled in—e.g., electro-optical, electro-mechanical, and electronic systems, etc.

Also, in some embodiments, computer 60 may be configured to receive particle count signals that also include information regarding the size of the particles detected from the particle counter 50. Based on such particle size distributions, computer 60 may also collect and analyze data related to the suitability of the components for assembly into their designated ultimate higher-level system based upon particle size.

In this way, computer 60, in conjunction with the particle detection environment 11, may be utilized to determine the suitability of component(s) for assembly into higher-level systems based upon the number and sizes of particles counted—such that components that do not meet pre-specified particle count and size characteristics may be screened and discarded from use in higher-level systems (e.g. electro-optical system, electro-mechanical system, and/or electronic system, etc.). As will be discussed, in one embodiment, these types of components may be utilized in storage devices, such as disk drives.

Various implementations of the particle monitoring system 2 and methods therefore will now be described in different embodiments and environments. It should be appreciated that the particle monitoring system 2 of the present invention may be used for removing contaminant particles from a component and characterizing the contaminant particles from the component that is to be subsequently utilized in a precision electronic, mechanical, electro-mechanical, and/or electro-optical system, etc. In one embodiment, the component may be utilized in a storage device, such as a disk drive.

Figure 2:
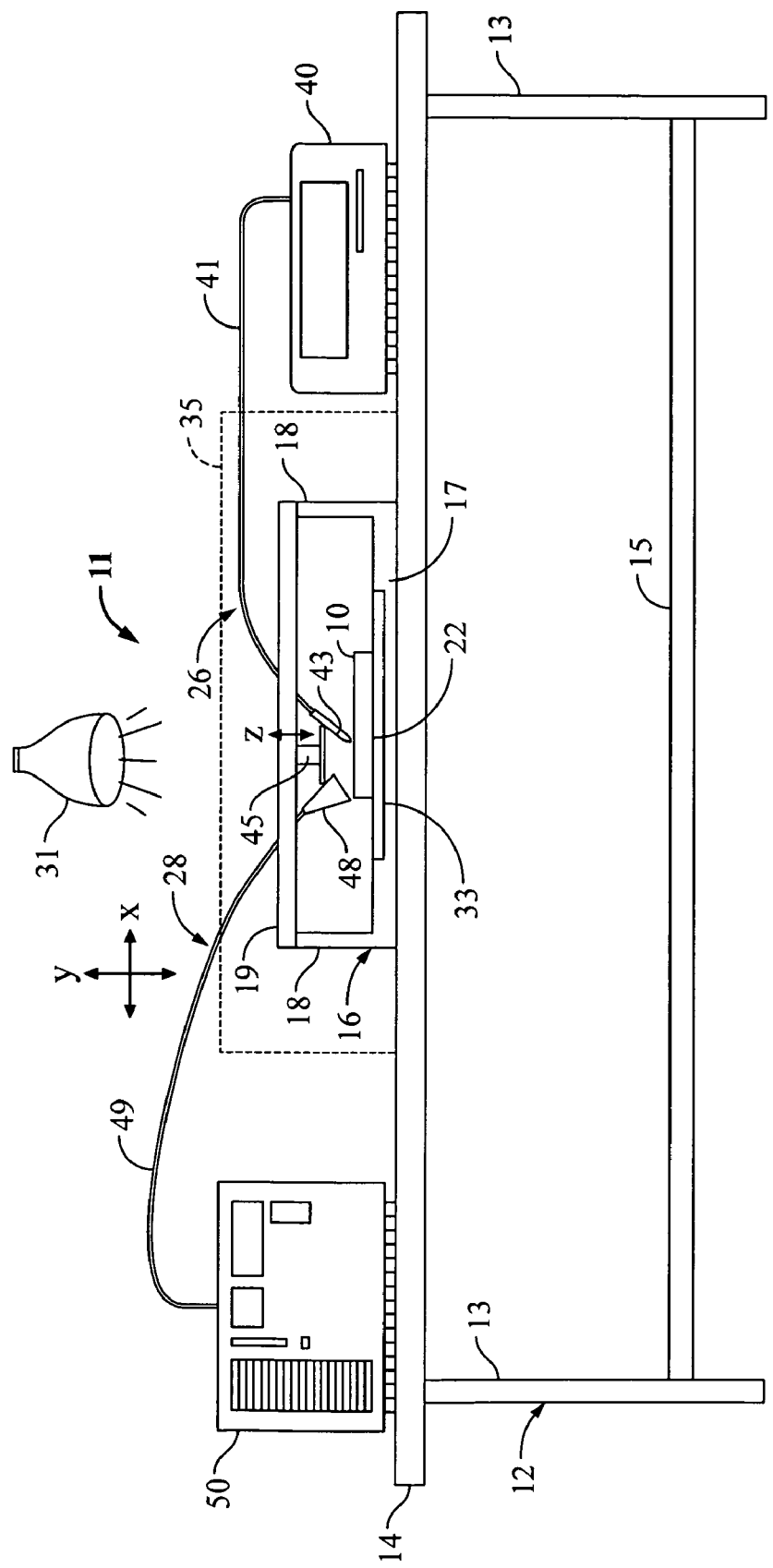
FIG. 2 is a side view of an exemplary particle detection environment of the particle monitoring system, according to one embodiment of the present invention.

Turning now to FIG. 2, FIG. 2 is a side view of an exemplary particle detection environment 11, according to one embodiment of the present invention. In this embodiment, the particle detection environment 11 is utilized as part of a clean-bench environment. As is known in the art, in a clean-bench environment, laminar air-flow is streamed over a bench 12 such that the particle detection environment 11 remains in a relatively clean environment.

As can be seen in FIG. 2, the snow generator 40, component 10, and particle counter 50, as previously discussed, are located on a table portion 14 of a bench 12 that includes parallely-opposed legs 13 and a cross-bar 15, for utilization in a clean-bench environment.

It should be appreciated that the clean-bench environment is only one type of environment that may be utilized with embodiments of the invention. In other embodiments, the particle detection environment 11 may be utilized in a clean-room or in other configurations utilizing sealed enclosures, as will be discussed, or may simply be utilized in a "non-clean" environment.

In this embodiment, the particle detection environment 11 includes a snow generator 40 configured to generate a continuous stream of cleaning snow including ice particles. The cleaning snow is emitted through jet spray device 26. Particularly, the cleaning snow is emitted through an orifice outlet (not particularly shown) of a nozzle 43 of the jet spray device 26 onto the component 10 mounted to a holding platform 17 to cause the ejection of contaminant particles from the component. The nozzle 43 and orifice of the jet spray device 26 may be held in a stationary position by a mounting device 45 locally relative to the component 10.

Similarly, the particle collection device 28 includes a collector 48 that is likewise disposed locally around the component 10 to directly collect contaminant particles ejected from the component 10 and is likewise held in a stationary position by mounting device 45.

In one embodiment, the collector 48 of the particle collection device 28 is funnel-shaped, and the particle collection device 28 further comprises a collection tube 49 coupled to the collector funnel 48 and the particle counter 50. The collector funnel 48 is disposed locally around the component 10 to directly collect particles ejected from the component 10 and the collection tube 49 is used to couple the collector funnel 48 to the particle counter 50 such that the particle counter 50 is in fluid communication with the collector funnel 49.

It should be appreciated that the collector being funnel-shaped is but only example. The collector may be of any suitable shape that can be located locally relative to the component to directly collect contaminant particles ejected from the component, such as any general circular shape, square shape, polygonal shape, etc. Also, in some embodiments the collector may substantially surround the component.

The mounting device 45 holds both the nozzle 43 of the jet spray device 26 and the collector funnel 48 in a fixed position relative to one another and to the component 10 allowing for the direct collection of particles ejected from the component. The mounting device 45, in one embodiment, may be T-shaped in cross-section, and is configured with suitable mounting openings to secure the jet nozzle 43 and the collector funnel 48 in place. The mounting device 45 may be made of a suitable plastic, polymer, or metallic material.

Also, in one embodiment, the collection tube 49 may have heater tape wrapped around it to aid in vaporizing residual cleaning snow. For example, the heater tape may be a type of commercially available tape that includes copper conductive elements such that the tape and the collection tube 49 may be heated to vaporize residual cleaning snow.

As previously described, particle counter 50 is coupled to and in fluid communication with collector funnel 48 via collection tube 49 such that particle counter 50 can directly count particles emitted from the component 10 that are collected locally by collector funnel 48. Particularly, particle counter 50 is operable to sample a pre-defined volume of gas (e.g. air) from particle collector funnel 48 in order to detect and count particles ejected from component 10.

For example, particle counter 50 may be a typical commercially-available programmable multi-channel airborne particle counter capable of measuring 0.1-5.0 micron particles at a programmable flow rate (e.g. 1 cubic foot per minute (CFM)). Particle counter 50 may include a vacuum and suitable control circuitry to implement this functionality, as should be appreciated by those of skill in the art. Particularly, particle counter 50 may be configured to sample a suitable volume of air at a suitable air-flow rate for a pre-determined amount of time.

For example, in one embodiment, particle counter 50 may include a photocell and an analog-to-digital (A/D) converter. In this example, when a particle passes between a light-emitter and a light-receiver of the photocell, a voltage drop occurs. This voltage drop is converted by the A/D converter into a particle count signal. As previously discussed, this particle count signal may be transmitted to a computer via a suitable connection for characterization purposes of the detected particles.

It should be appreciated that various types of standard commercially-available particle counters may be utilized for this purpose and are well known in the art. The previously-described particle counter is but one example.

Looking back to snow generator 40, snow generator 40 may be configured to generate a continuous stream of cleaning snow including ice particles, in which the cleaning snow is emitted from the orifice outlet (not particularly shown) of the jet nozzle 43 of the jet spray device 26 onto the component 10 to cause the ejection of particles from the component. In one embodiment, the cleaning snow comprises carbon dioxide ice particles.

This carbon dioxide cleaning process utilizing $CO_2$ snow is based upon the expansion of either liquid or gaseous carbon dioxide through the orifice of the jet nozzle 43 of the jet spray device 26. Carbon dioxide exiting the orifice expands and forms $CO_2$ snow particles and a high velocity gas-carrier stream. Upon impact with the surface of the substrate 10 and the contaminant particles thereon, the $CO_2$ snow impacts the surface of the component 10 and removes micron and submicron contaminant particles by momentum transfer and the snow sublimes back to a gas. Hydrocarbons are also removed. The high-velocity gas blows the contaminant particles away into the collector funnel 48 for counting by particle counter 50. It should be appreciated that the carbon dioxide snow generator 40 is adjustable as to the snow particle size and flow rate as well as the propellant temperature and flow rate.

As will be described, the orifice of the jet nozzle 43 may be moved and directed to cover a defined surface, surface area, and angle, etc., relative to the component 10. By also placing the collector funnel 48 at a specific angle of reflection in spaced-apart relation from the orifice of the jet nozzle 43, quantitative particle cleanliness data from contaminant particles can be obtained and counted by the particle counter 50, and this data can be further characterized by computer 60.

It should also be appreciated that the size of the orifice and the nozzle configuration of the jet spray device 26 may be adjusted to obtain desired $CO_2$ snow characteristics. Thus, a jet of high velocity snow flakes may be produced and directed at the surface of the component 10 to be cleaned. The velocity may be adjusted to achieve maximum cleaning efficiency while causing minimal surface damage. The particle sizes of the carbon dioxide ice entrained in the snow stream may also be varied depending upon the surface of the component to be cleaned and the contaminants to be removed.

However, it should be appreciated that other types of gases besides carbon dioxide may be utilized, such as, nitrogen, argon, or neon. Although, presently, the use of carbon dioxide is utilized because of its relatively low cost in comparison to other gases and because of its environmentally desirable properties.

In one embodiment, the particle detection environment 11 may further include a robotic X-Y table 16 that includes the holding platform 17 to mount the component 10. The component 10 may be mounted to holding platform 17 by conventional methods such as locator pins, clamps, clips, etc. It should be appreciated that any suitable sort of releasable attachment devices may be utilized to attach the component 10 to be cleaned to the holding platform 17 dependent upon the type of component to be cleaned.

The robotic X-Y table 16 includes a pair of parallely-opposed guide rails 18 and a movable robotic arm 19 that may be robotically moved in bi-directional horizontal directions (denoted X, Y in FIG. 2) relative to the guide arms 18. It should be appreciated that robotic X-Y tables are well known to those of skill in the art.

Mounting device 45 may be fixedly attached to the robotic arm 19. Mounting device 45 holds jet nozzle 43 and collector funnel 48 in a fixed position such that jet nozzle 43 and collector funnel 48 move with robotic arm 19 relative to component 10 mounted to holding platform 17. Mounting device 45 may also be adjustable in the vertical Z-direction (as indicated in FIG. 2) relative to component 10 such that collector funnel 48 and jet nozzle 43 may be manually moved in vertical Z-direction relative to the component 10. It should be appreciated that the mounting device 45 may be manually moved relative to robotic arm 19 in the vertical Z-direction and then fixed in position to robotic arm 19 at a specific height relative to component 10. Alternatively, in another embodiment, the mounting device 45 itself may be expandable and retractable such that in can be moved in the vertical Z-direction and set to a specific height relative to component 10.

In particular, with this configuration, the robotic X-Y table 16 is configured to allow for the movement of the jet nozzle 43 and the collector funnel 48 in bi-directional horizontal directions (X-Y directions) relative to the component 10, as well as, in the vertical Z-direction relative to the component 10.

In one embodiment, the robotic X-Y table 16 may be pre-programmed to implement a series of bi-directional horizontal movements (X, Y directions) of the jet nozzle 43 and the collector funnel 48 relative to the component 10. In this way, component 10 may be sprayed and cleaned by jet nozzle 43, and particles directly collected by collector funnel 48, and the jet spray of $CO_2$ snow can cover a pre-determined surface area, in a pre-determined period of time, at a predetermined rate of speed.

Also, in some embodiments, a heat source may be used to heat the component 10 to aid in the cleaning of component 10 and to aid in the evaporation of cleaning snow. For example, a heater, such as an infrared heat lamp 31 may be located above the component 10 in order to provide for the heating of the component 10. Alternatively, a heating element, such as a heating plate 33 may be disposed in the holding platform 17 in direct contact with the component 10, such that the component 10 may be directly heated.

As previously described, mounting device 45 may be utilized to adjust the collector funnel 48 and the jet spray nozzle 43 height in the vertical Z-direction relative to the component 10. Further, mounting device 45 may also be utilized to adjust the angle of each of the collector funnel 48 and the jet spray nozzle 43, respectively.

Thus, in operation, snow generator 40 may generate a continuous stream of cleaning snow including $CO_2$ ice particles that are emitted from the outlet orifice of jet nozzle 43 of the jet spray device 26 onto component 10 to cause the ejection of contaminant particles from the component.

The robotic X-Y table may be programmed to move both the jet nozzle 43 and the collector funnel 48 in unison in a pre-programmed serious of bi-directional horizontal movements (X,Y) relative to component 10. Further, as previously discussed, both the collector funnel 48 and the jet nozzle 43 may be adjusted relative to component 10 in the vertical Z-direction by mounting device 45, as well as, in their respective angles relative to component 10. Additionally, the robotic X-Y table's horizontal movements may also be programmable as to the speed at which the jet nozzle 43 and collector funnel 48 move relative to component 10.

In this way, component 10 may be directly cleaned by jet nozzle 43 of jet spray device 26, and particles directly collected by collector funnel 48, wherein the jet spray of $CO_2$ snow covers a pre-determined surface area of the component 10, in a pre-determined period of time, at a pre-determined rate of speed. Further, both the height in the vertical Z-direction of the jet nozzle 43 and the collector funnel 48, and their respective angles, relative to the component 10, are adjustable by the mounting device 45. This provides a very flexible process of cleaning a component 10 and directly collecting contaminant particles ejected therefrom during cleaning.

During the pre-programmed movements of the robotic X-Y table, particle counter 50 is utilized to sample a predefined volume of gas (e.g. air) from collector funnel 48 via collector tube 49 and is utilized to detect and count the contaminant particles ejected locally from the component 10.

It should be appreciated that with this previously-described configuration of the particle detection environment 11, because the collector funnel 48 and the jet spray nozzle 43 are directly located proximate to one another and the component 10, that contaminant particles are directly measured as they are ejected from the surface of the component 10 as the $CO_2$ snow impacts and rapidly sublimes to a gas. This provides for improved particle counting accuracy and reproducibility.

Further, because of the spaced-apart configuration of the jet spray nozzle 43 and the collector funnel 48, in conjunction with their synchronous moveability provided by the robotic X-Y table 16, in conjunction with the fact that robotic X-Y table 16 may be pre-programmed to provide optimized cleaning movement routines for particular components, an optimized and efficient cleaning process for components utilizing $CO_2$ snow is provided. Moreover, this process is repeatable and the use of the $CO_2$ snow provides little risk of damage and erosion to the component being cleaned.

Additionally, the capturing, counting, and measuring of the particles ejected from the component 10 enables consistent measurement and control of component cleanliness. As previously described, due to the jet spray nozzle 43 and collector funnel 48 being located proximate to the component 10, and to one another, ejected particles are directly collected resulting in a highly accurate particle collection process.

Although a particular embodiment has been described as an example with reference to FIG. 2, it should be appreciated that other embodiments and variations fall within the scope of the present invention. For example, instead of the particle detection environment 11 being utilized in conjunction with a clean-bench, the particle detection environment may just as easily be utilized in a clean room environment.

Alternatively, in one embodiment, instead of being located in a clean-bench environment, the robotic X-Y table 16 and the component 10 contained therein may be placed within a sealed enclosure 35 (indicated by dash lines) in which tubes 41 and 49 from the snow generator 40 and particle counter 50, respectively, extend into the sealed enclosure 35. The sealed enclosure 35 may also be under vacuum pressure. This provides a very clean environment for accurate contaminant particle counting.

Additionally, in other embodiments, instead of utilizing only one collector 48, the particle collection device 28 may comprise a plurality of collectors. For example, a plurality of collector funnels may be positioned in an angular distribution around the component 10, wherein each collector funnel is respectively coupled to a collection tube to couple each collector funnel with the particle counter 50, respectively, such that each collector funnel is in fluid communication with the particle counter 50. In this way, particles can be detected simultaneously, at various angularly disposed locations, relative to the component 10.

As previously described, a computer 60 (see FIG. 1) may optionally be coupled to the particle counter 50 in order to characterize information related to the particles counted by the particle counter 50. Particularly, computer 60 may be configured to detect particle count signals received from particle counter 50 over a suitable connection and interface, in which each particle count signal corresponds to a particle detected by the particle counter 50.

For example, based upon received particle count signals for one or more particular components that are cleaned, computer 60 may characterize this data to determine if the individual component, or the plurality components, on average, are sufficiently clean enough to be used in higher-level assemblies for which they are to be assembled in—e.g., electro-optical, electro-mechanical, and electronic systems, etc.

Also, in some embodiments, computer 60 may be configured to receive particle count signals that also include information regarding the size of the particles detected from the particle counter 50. Based on such particle size distributions, computer 60 may also collect and analyze data related to the suitability of the components for assembly into their designated ultimate higher-level system based upon particle size.

In this way, computer 60, in conjunction with the particle detection environment 11, may be utilized to determine the suitability of component(s) for assembly into higher-level systems based upon the number and sizes of particles counted—such that components that do not meet pre-specified particle count and size characteristics may be screened and discarded from use in higher-level systems (e.g. electro-optical system, electro-mechanical system, and/or electronic system, etc.).

It should be appreciated that computer 60 may be any type of computing device, such as a personal computer (PC) running, for example, a LINUX operating system or a MICROSOFT operating system, such as a WINDOWS type operating system. Computer 60 may include a suitable processor, memory, and suitable I/O interfaces to implement the various embodiments of the invention related to characterizing particles counted based on number and size. In another embodiment, the computer may simply comprise a processor, memory and appropriate control code integrated into the particle detector.

In other embodiments, commercially available devices to perform both the previously-described functionality of particle counter 50 and computer 60 may be utilized. For example, specialized commercially available spectrometers having advanced computing capabilities may be utilized to perform particle counting functions (e.g., count the particles, size the particles, chemically analyze the particles, and perform other analysis functions), as well as computational functions (e.g., perform statistical analysis of the counted particles). Such devices may be programmable to implement the previously-described functions performed by computer 60. As an example, one such commercially available spectrometer is called the Aerosol Time-of-Flight Mass Spectrometer (ATOFMS), model 3800, sold by TSI Inc.

Components of the various embodiments of the invention may be implemented as hardware, software, firmware, microcode, or any combination thereof. When implemented in software, firmware, or microcode, the elements of the embodiment of the present invention are the program code or code segments that include instructions to perform the necessary tasks. A code segment may represent a procedure, a function, a subprogram, a program, a routine, a subroutine, a module, a software package, a class, or any combination of instructions, data structures, or program statements.

The program or code segments may be stored in a computer or processor readable medium or transmitted by a computer data signal embodied in a carrier wave, or a signal modulated by a carrier, over a transmission medium. The "processor readable or accessible medium" or "computer readable or accessible medium" may include any medium that can store, transmit, or transfer information. Examples of computer accessible media include an electronic circuit, a semiconductor memory device, a read only memory (ROM), a flash memory, an erasable ROM (EROM), a floppy diskette, a compact disk (CD-ROM), an optical disk, a hard disk, a fiber optic medium, a radio frequency (RF) link, etc. The code segments may be downloaded via computer networks such as the Internet, Intranet, etc. The computer accessible medium may include data that, when accessed by a computer, cause the computer to perform the operations described herein. The term "data" herein refers to any type of information that is encoded for machine-readable purposes. Therefore, it may include programs, code, data, files, etc.

Figure 3:
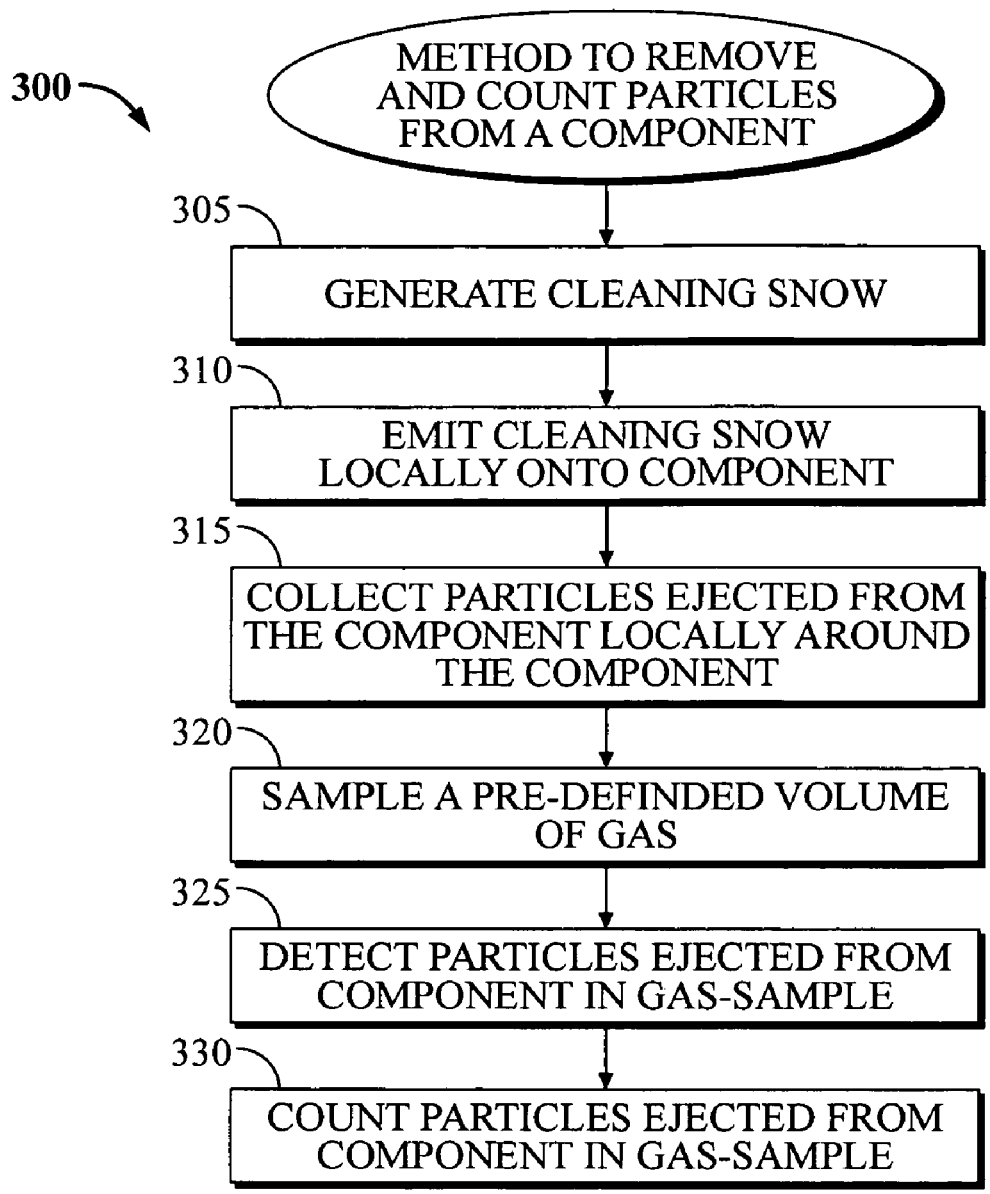
FIG. 3 is a flow diagram illustrating a method to remove and count particles from a component, according to one embodiment of the present invention.

With reference to FIG. 3, FIG. 3 is a flow diagram illustrating a method 300 to remove and count particles from a component, according to one embodiment of the present invention. At block 305, cleaning snow is generated. At block 310 the cleaning snow is emitted locally onto the component. Particles ejected from the component are collected locally around the component (block 315).

Next, a pre-defined volume of gas (e.g. air) is sampled (block 320). The particles ejected from the component in the gas sample are detected at block 325. Lastly, at block 330, the particles ejected from the component in the gas-sample are counted.

Although the previously-described system and method to remove and count particles from a component has been generally described as being utilized to remove and count particles from any type of component, in one embodiment, components from a storage device, such as a disk drive, may be cleaned by the system and method previously-described.

Figure 4:
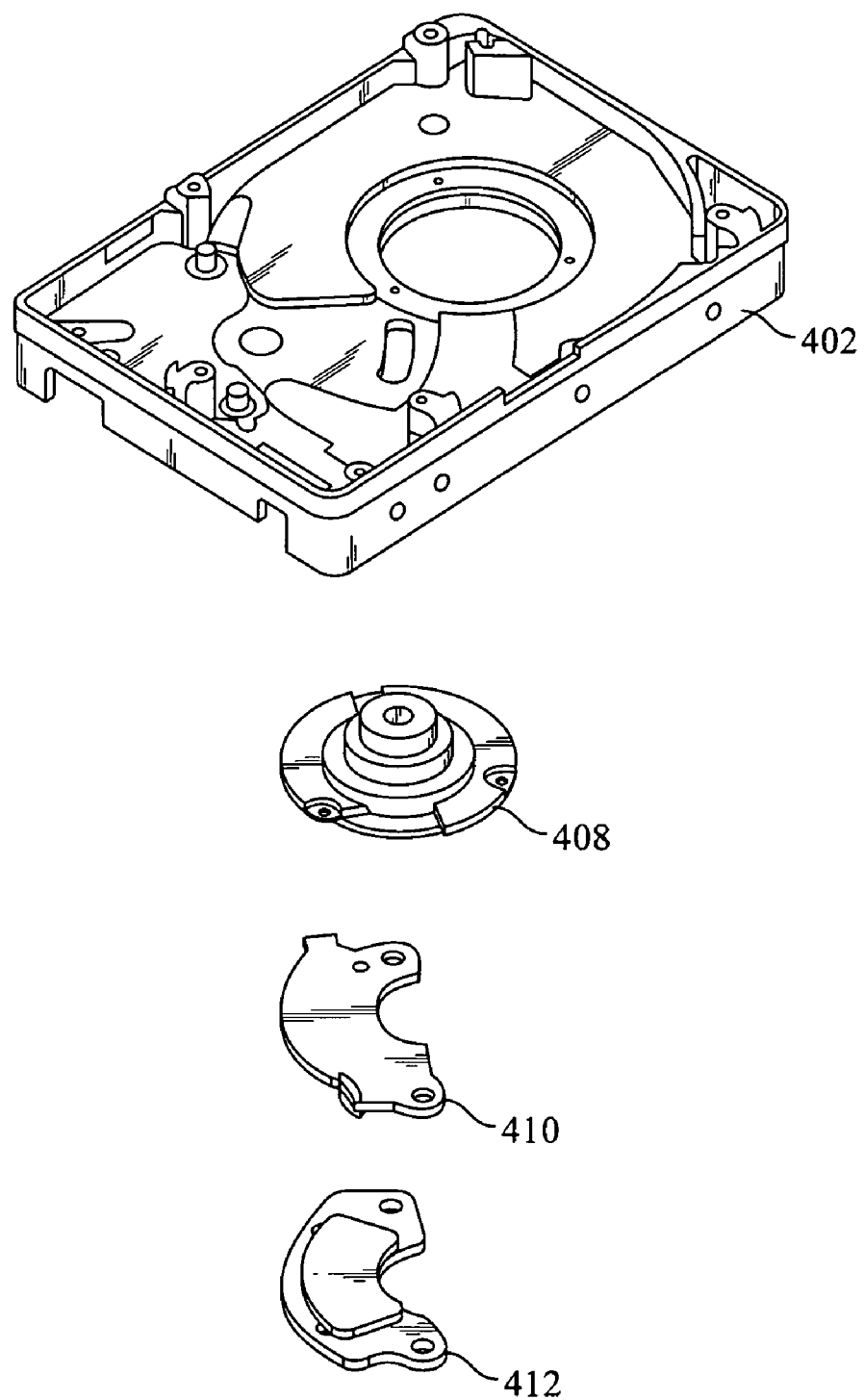
FIG. 4 is a perspective view of components of a disk drive that may be cleaned, according to one embodiment of the present invention.

For example, with reference to FIG. 4, FIG. 4 is a perspective view of components of a disk drive that may be cleaned utilizing the previously-described system and method to remove and count particles.

For example, a voice coil motor (VCM) plate 410 or 412 of a disk drive may be attached to the holding platform 17 of the robotic X-Y table 16 of the particle monitoring system 2 and may be cleaned in accordance with the previously described system and method, and the ejected contaminant particles counted.

Other types of disk drive components such as a spindle motor 408 or a base 402 of a disk drive may also be cleaned in a similar fashion. It should be appreciated that almost any type of mechanical or electromechanical component from a disk drive may be cleaned in accordance with the previously-described system and method to remove and count particles including: clamps, spacers, interposers, etc.

However, it should be appreciated that these illustrated disk drive components are just one type of component that can be cleaned, utilizing the previously-described system and method of the invention, and that any type of electro-optical, electro-mechanical, and/or electronic component, etc., may be cleaned and the particles ejected therefrom counted utilizing the embodiments of the invention.

It should be appreciated by those with skill in this art that, although embodiments of the invention have been previously described with reference to particular structural implementations such as utilizing tubes, particle counters, particle detection devices, jet spray devices, and snow generators, that the embodiments of the invention may be utilized with a wide variety of different types of test and component cleaning equipment, and in different sorts of environments, in order to remove and count particles from a component.

We claim:

1. A particle monitoring system to monitor particles removed from a component, the particle monitoring system comprising:
   a jet spray device having an outlet that is disposed locally relative to the component;
   a snow generator operable to generate cleaning snow comprising a stream of ice particles, wherein the cleaning snow is emitted from the outlet of the jet spray device onto the component to cause the ejection of particles from the component;
   a particle collection device having a collector that is disposed locally around the component to collect particles ejected from the component;
   a particle counter coupled to and in fluid communication with the particle collection device, the particle counter operable to detect and count particles ejected from the component; and
   a robotic X-Y table configured to allow for the movement of the jet spray device and the particle collection device in bi-directional horizontal directions relative to the component.

2. The particle monitoring system of claim 1, wherein the particle counter is configured to sample a pre-defined volume of gas from the particle collection device.

3. The particle monitoring system of claim 2, wherein the snow generator is configured to generate a continuous stream of cleaning snow.

4. The particle monitoring system of claim 1, wherein the cleaning snow comprises carbon dioxide ice particles.

5. The particle monitoring system of claim 4, wherein the collector comprises a collector funnel and the particle collection device further comprises a collection tube coupled to the collector funnel to couple the collector funnel with the particle counter such that the collector funnel is in fluid communication with the particle counter.

6. The particle monitoring system of claim 5, wherein the collection tube includes heater tape to vaporize residual cleaning snow.

7. The particle monitoring system of claim 1, wherein the robotic X-Y table is programmable to implement a pre-programmed series of bi-directional horizontal movements of the jet spray device and the particle collection device.

8. The particle monitoring system of claim 1, wherein the component is a disk drive component.

9. The particle monitoring system of claim 1, wherein the collector substantially surrounds the component.

10. The particle monitoring system of claim 1, wherein the collector comprises a plurality of collectors positioned in an angular distribution around the component, each collector being respectively coupled to a collection tube to couple each collector with a particle counter such that each collector is in fluid communication with a particle counter.

11. The particle monitoring system of claim 1, further comprising a heat source to eat the component.

12. The particle monitoring system of claim 11, wherein the heat source is a heating plate.

13. The particle monitoring system of claim 11, wherein the heat source is a heat lamp.

14. A particle monitoring system to monitor particles removed from a component, the particle monitoring system comprising:
- a jet spray device having an outlet that is disposed locally relative to the component;
- a snow generator configured to generate a continuous stream of cleaning snow including ice particles, wherein the cleaning snow is emitted from the outlet of the jet spray device onto the component to cause the ejection of particles from the component;
- a particle collection device having a collector that is disposed locally around the component to collect particles ejected from the component;
- a robotic X-Y table including a holding platform to hold the component, the robotic X-Y table configured to allow for the movement of the jet spray device and the particle collection device in bi-directional horizontal directions relative to the component;
- a heat source to heat the component; and
- a particle counter coupled to and in fluid communication with the particle collection device, the particle counter operable to sample a pre-defined volume of gas from the particle collection device and to detect and count particles ejected from the component.

15. The particle monitoring system of claim 14, wherein the cleaning snow comprises carbon dioxide ice particles.

16. The particle monitoring system of claim 14, wherein the collector comprises a collector funnel and the particle collection device further comprises a collection tube coupled to the collector funnel, the collector funnel disposed locally around the component to directly collect particles ejected from the component and the collection tube to couple the collector funnel to the particle counter such that the particle counter is in fluid communication with the collector funnel.

17. The particle monitoring system of claim 16, wherein the collection tube includes heater tape to vaporize residual cleaning snow.

18. The particle monitoring system of claim 14, wherein the robotic X-Y table is programmable to implement a pre-programmed series of bi-directional horizontal movements of the jet spray device and the particle collection device.

19. The particle monitoring system of claim 14, wherein the component is a disk drive component.

20. The particle monitoring system of claim 14, wherein the heat source is a heating plate.

21. The particle monitoring system of claim 14, wherein the heat source is a heat lamp.

22. A particle monitoring system to monitor particles removed from a component, the particle monitoring system comprising:
- a jet spray device having an outlet that is disposed locally relative to the component;
- a snow generator operable to generate cleaning snow comprising a stream of ice particles, wherein the cleaning snow is emitted from the outlet of the jet spray device onto the component to cause the ejection of particles from the component;
- a particle collection device having a collector that is disposed locally around the component to collect particles ejected from the component, wherein the collector comprises a collector funnel and the particle collection device comprises a collection tube including heater tape to vaporize residual cleaning snow coupled to the collector funnel to couple the collector funnel with the particle counter such that the collector funnel is in fluid communication with the particle counter; and
- a particle counter coupled to and in fluid communication with the particle collection device, the particle counter operable to detect and count particles ejected from the component.

23. The particle monitoring system of claim 22, wherein the particle counter is configured to sample a pre-defined volume of gas from the particle collection device.

24. The particle monitoring system of claim 23, wherein the snow generator is configured to generate a continuous stream of cleaning snow.

25. The particle monitoring system of claim 22, wherein the cleaning snow comprises carbon dioxide ice particles.

26. The particle monitoring system of claim 22, further comprising a robotic X-Y table configured to allow for the movement of the jet spray device and the particle collection device in bi-directional horizontal directions relative to the component.

27. The particle monitoring system of claim 26, wherein the robotic X-Y table is programmable to implement a pre-programmed series of bi-directional horizontal movements of the jet spray device and the particle collection device.

28. The particle monitoring system of claim 22, wherein the component is a disk drive component.

29. The particle monitoring system of claim 22, wherein the collector substantially surrounds the component.

30. The particle monitoring system of claim 22, wherein the collector comprises a plurality of collectors positioned in an angular distribution around the component, each collector being respectively coupled to a collection tube to couple each collector with a particle counter such that each collector is in fluid communication with a particle counter.

31. The particle monitoring system of claim 22, further comprising a heat source to heat the component.

32. The particle monitoring system of claim 31, wherein the heat source is a heating plate.

33. The particle monitoring system of claim 31, wherein the heat source is a heat lamp.

* * * * *